US009303232B2

(12) United States Patent
Denutte et al.

(10) Patent No.: US 9,303,232 B2
(45) Date of Patent: Apr. 5, 2016

(54) PERFUME SYSTEMS

(71) Applicant: The Procter & Gamble Company, Cincinnati, OH (US)

(72) Inventors: Hugo Robert Germain Denutte, Aalst (BE); An Pintens, Brasschaat (BE); Johan Smets, Lubbeek (BE); Freek Annie Camiel Vrielynck, Beernem (BE); Koen Van Aken, Kuurne (BE)

(73) Assignee: The Procter & Gamble Company, Cincinnati, OH (US)

( * ) Notice: Subject to any disclaimer, the term of this patent is extended or adjusted under 35 U.S.C. 154(b) by 77 days.

(21) Appl. No.: 14/096,041

(22) Filed: Dec. 4, 2013

(65) Prior Publication Data

US 2014/0161740 A1 Jun. 12, 2014

Related U.S. Application Data

(60) Provisional application No. 61/734,011, filed on Dec. 6, 2012.

(51) Int. Cl.

| | |
|---|---|
| *C11B 9/00* | (2006.01) |
| *A61K 8/49* | (2006.01) |
| *A61Q 5/02* | (2006.01) |
| *A61Q 11/00* | (2006.01) |
| *C11D 3/50* | (2006.01) |
| *C07D 493/08* | (2006.01) |
| *A61Q 13/00* | (2006.01) |
| *C11D 3/20* | (2006.01) |
| *C11D 11/00* | (2006.01) |

(52) U.S. Cl.
CPC ............... *C11B 9/008* (2013.01); *A61K 8/498* (2013.01); *A61K 8/4973* (2013.01); *A61Q 5/02* (2013.01); *A61Q 11/00* (2013.01); *A61Q 13/00* (2013.01); *C07D 493/08* (2013.01); *C11B 9/0076* (2013.01); *C11D 3/2096* (2013.01); *C11D 3/505* (2013.01); *C11D 11/0017* (2013.01)

(58) Field of Classification Search
None
See application file for complete search history.

(56) References Cited

U.S. PATENT DOCUMENTS

| | | | |
|---|---|---|---|
| 4,224,176 A * | 9/1980 | Sprecker | C11D 3/50 510/103 |
| 4,250,099 A | 2/1981 | Kaiser | |
| 4,263,208 A | 4/1981 | Sprecker et al. | |
| 4,430,243 A | 2/1984 | Bragg | |
| 5,240,908 A * | 8/1993 | Narula | C11B 9/008 512/13 |
| 5,576,282 A | 11/1996 | Miracle et al. | |
| 5,597,936 A | 1/1997 | Perkins et al. | |
| 5,651,976 A | 7/1997 | Price et al. | |
| 6,020,303 A | 2/2000 | Cripe et al. | |
| 6,060,443 A | 5/2000 | Cripe et al. | |
| 6,225,464 B1 | 5/2001 | Hiler, II et al. | |
| 6,326,348 B1 | 12/2001 | Vinson et al. | |
| 6,458,754 B1 | 10/2002 | Velazquez et al. | |
| 7,119,060 B2 | 10/2006 | Shefer et al. | |
| 2004/0110648 A1 | 6/2004 | Jordan, IV et al. | |
| 2005/0003980 A1 | 1/2005 | Baker et al. | |
| 2007/0275866 A1 | 11/2007 | Dykstra | |
| 2008/0139447 A1 | 6/2008 | Narula et al. | |
| 2008/0305977 A1 | 12/2008 | Smets et al. | |
| 2010/0287710 A1 * | 11/2010 | Denutte | C11D 17/0039 8/137 |

OTHER PUBLICATIONS

International Search Report; International Application No. PCT/US2013/073206; date of mailing Apr. 23, 2014; 4 pages.
International Search Report; International Application No. PCT/US2013/073207; date of mailing Apr. 4, 2014; 4 pages.
Hansch and Leo ( cf., A. Leo, in Comprehensive Medicinal Chemistry, vol. 4, C. Hansch, P. G. Sammens, J. B. Taylor and C. A. Ramsden, Eds., pp. 295-319, Pergamon Press, 1990.
ASTM method D2887-04a, "Standard Test Method for Boiling Range Distribution of Petroleum Fractions by Gas Chromatography," ASTM International.
U.S. Appl. No. 14/096,043, filed Dec. 4, 2013, Denutte, et al.

* cited by examiner

*Primary Examiner* — Frederick Krass
*Assistant Examiner* — Michael P Cohen
(74) *Attorney, Agent, or Firm* — James F. McBride; Steven W. Miller

(57) ABSTRACT

The present application relates to perfume raw materials, perfume delivery systems and consumer products comprising such perfume raw materials and/or such perfume delivery systems, as well as processes for making and using such perfume raw materials, perfume delivery systems and consumer products. Such perfume raw materials and compositions, including the delivery systems, disclosed herein expand the perfume communities' options as such perfume raw materials can provide variations on character and such compositions can provide desired odor profiles.

15 Claims, No Drawings

PERFUME SYSTEMS

FIELD OF INVENTION

The present application relates to perfume raw materials, perfume delivery systems and consumer products comprising such perfume raw materials and/or perfume delivery systems, as well as processes for making and using such perfume raw materials, perfume delivery systems and consumer products.

BACKGROUND OF THE INVENTION

Consumer products may comprise one or more perfumes, and/or perfume delivery systems that can mask an undesirable odor and/or provide a desired scent and/or experience to a product and/or a situs that is contacted with such a product. While current perfumes, and perfume delivery systems provide desirable experiences and/or fragrances, consumers continue to seek products that contain sensates, such as cooling or have scents that may be longer lasting and that are tailored to their individual desires (see for example USPA 2007/0275866 A1 and USPA 2008/0305977 A1)—unfortunately the pool of perfume raw materials and perfume delivery systems that is available is still too limited to completely meet the desired needs.

Applicants believe that the perfume raw materials and perfumes, including the delivery systems, disclosed herein expand the options, as such sensates and/or perfume raw materials can provide variations on character and such and/or perfumes can provide desired sensations and/or odor profiles. In certain aspects, such and/or perfume raw materials and/or perfume delivery systems comprising such and/or perfume raw materials may provide variations on character, sensation and/or odor profiles that are better than expected as measured by parameters such as headspace analysis (employed to determine perfume delivery system perfume leakage and/or perfume delivery efficiency), C log P, boiling point and/or odor detection threshold.

SUMMARY OF THE INVENTION

The present application relates to perfume raw materials, perfume delivery systems and consumer products comprising such perfume raw materials and/or such perfume delivery systems, as well as processes for making and using such perfume raw materials, perfume delivery systems and consumer products.

DETAILED DESCRIPTION OF THE INVENTION

Definitions

As used herein "consumer product" means baby care, beauty care, fabric & home care, family care, feminine care, health care, snack and/or beverage products or devices generally intended to be used or consumed in the form in which it is sold. Such products include but are not limited to diapers, bibs, wipes; products for and/or methods relating to treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use including fine fragrances; and shaving products, products for and/or methods relating to treating fabrics, hard surfaces and any other surfaces in the area of fabric and home care, including: air care including air fresheners and scent delivery systems, car care, dishwashing, fabric conditioning (including softening and/or freshening), laundry detergency, laundry and rinse additive and/or care, hard surface cleaning and/or treatment including floor and toilet bowl cleaners, and other cleaning for consumer or institutional use; products and/or methods relating to bath tissue, facial tissue, paper handkerchiefs, and/or paper towels; tampons, feminine napkins; products and/or methods relating to oral care including toothpastes, tooth gels, tooth rinses, denture adhesives, tooth whitening; over-the-counter health care including cough and cold remedies, pain relievers, RX pharmaceuticals, pet health and nutrition; processed food products intended primarily for consumption between customary meals or as a meal accompaniment (non-limiting examples include potato chips, tortilla chips, popcorn, pretzels, corn chips, cereal bars, vegetable chips or crisps, snack mixes, party mixes, multigrain chips, snack crackers, cheese snacks, pork rinds, corn snacks, pellet snacks, extruded snacks and bagel chips); and coffee.

As used herein, the term "cleaning and/or treatment composition" is a subset of consumer products that includes, unless otherwise indicated, beauty care, fabric & home care products. Such products include, but are not limited to, products for treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use including fine fragrances; and shaving products, products for treating fabrics, hard surfaces and any other surfaces in the area of fabric and home care, including: air care including air fresheners and scent delivery systems, car care, dishwashing, fabric conditioning (including softening and/or freshening), laundry detergency, laundry and rinse additive and/or care, hard surface cleaning and/or treatment including floor and toilet bowl cleaners, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, dentifrice, car or carpet shampoos, bathroom cleaners including toilet bowl cleaners; hair shampoos and hair-rinses; shower gels, fine fragrances and foam baths and metal cleaners; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists all for consumer or/and institutional use; and/or methods relating to oral care including toothpastes, tooth gels, tooth rinses, denture adhesives, tooth whitening.

As used herein, the term "fabric and/or hard surface cleaning and/or treatment composition" is a subset of cleaning and treatment compositions that includes, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, car or carpet shampoos, bathroom cleaners including toilet bowl cleaners; and metal cleaners, fabric conditioning products including softening and/or freshening that may be in liquid, solid and/or dryer sheet form; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists. All of such products which were applicable may be in standard, concentrated or even highly concentrated form even to the extent that such products may in certain aspect be non-aqueous.

As used herein, the term "oral care composition" is a product, which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity. The oral care composition may be in various forms including toothpaste, dentifrice, tooth gel, subgingival gel, mouthrinse, mousse, foam, mouthspray, lozenge, chewable tablet, chewing gum or denture product. The oral care composition may also be incorporated onto strips or films for direct application or attachment to oral surfaces. The term "dentifrice", as used herein, includes paste, gel, or liquid formulations unless otherwise specified.
The dentifrice composition may be a single phase composition or may be a combination of two or more separate dentifrice compositions. The dentifrice composition may be in any desired form, such as deep striped, surface striped, multilayered, having a gel surrounding a paste, or any combination thereof. Each dentifrice composition in a dentifrice comprising two or more separate dentifrice compositions may be contained in a physically separated compartment of a dispenser and dispensed side-by-side.

As used herein, articles such as "a" and "an" when used in a claim, are understood to mean one or more of what is claimed or described.

As used herein, the terms "include", "includes" and "including" are meant to be non-limiting.

As used herein, the term "solid" includes granular, powder, bar and tablet product forms.

As used herein, the term "fluid" includes liquid, gel, paste and gas product forms.

As used herein, the term "situs" includes paper products, fabrics, garments, hard surfaces, hair and skin.

As used herein, "perfume raw materials" include molecules that can serve the purposes of providing odour and/or a sensation such as cooling.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The PRMs disclosed herein (a.k.a., molecules) may provide one or more of the following benefits at levels that Applicants believe are unexpected in view of PRMs in general: a cooling sensation, neat product odor; wet fabric odor when applied to a fabric; dry fabric odor when applied to a fabric; reduced leakage from an encapsulate, including an encapsulate such as a perfume microcapsule; increased head space versus neat oil in certain perfume delivery technologies; odor when used in a matrix perfume delivery that is applied to a package; neat product odor when applied to a cleaning and/or treatment composition; fine fragrance composition odor when used in a fine fragrance; dry hair odor when a composition comprising such a PRM is applied to hair; PRM bloom from a solution comprising such a PRM; and new PRM character when applied to a situs. Confirmation of such benefits can be obtained by applying standard test methodologies detailed herein. The PRMs and stereoisomers of such PRMs above can be made in accordance with the teachings detailed in the present specification.

Molecules having Structure 1 or Structure 2 below and stereoisomers of such molecules are disclosed.

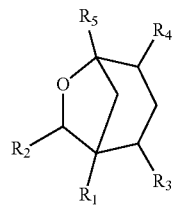

Structure 1

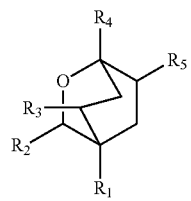

Structure 2

For Structure 1:
$R_1$, $R_4$ and $R_5$ are each independently selected from the group consisting of: a straight or branched $C_1$-$C_6$ alkyl moiety; a straight or branched $C_2$-$C_6$ alkenyl moiety; and a straight or branched $C_2$-$C_6$ alkyne moiety; and $R_2$ and $R_3$ are each independently selected from the group consisting of: hydrogen; a straight or branched $C_1$-$C_6$ alkyl moiety; a straight or branched $C_2$-$C_6$ alkenyl moiety; and a straight or branched $C_2$-$C_6$ alkyne moiety.

For Structure 2:
$R_1$, $R_2$, $R_3$ and $R_4$ are each independently selected from the group consisting of: hydrogen; a straight or branched $C_1$-$C_6$ alkyl moiety; a straight or branched $C_2$-$C_6$ alkenyl moiety; and a straight or branched $C_2$-$C_6$ alkyne moiety; and $R_5$ is selected from the group consisting of a straight or branched $C_1$-$C_6$ alkyl moiety;
a straight or branched $C_2$-$C_6$ alkenyl moiety; and a straight or branched $C_2$-$C_6$ alkyne moiety.

In one aspect, a composition comprising, based on total composition weight, at least 0.00001%, from about 0.001% to about 95%, from about 0.01% to about 85%, from about 0.01% to about 75%, from about 0.01% to about 65%, from about 0.01% to about 50%, from about 0.1% to about 15%, from about 0.1% to about 10% or even from about 0.5% to about 10% of one or more molecules having a structure according to Structure 1 and/or Structure 2 and an optional adjunct material is disclosed.

In one aspect, said composition comprises, based on total composition weight, at least 0.001%, from about 0.001% to about 5%, from 0.005% to about 4%, or even from 0.010% to about 2% of one or more molecules having a structure according to Structure 1 and/or Structure 2 and an adjunct ingredient selected from the group consisting of stannous, zinc, potassium, calcium, or copper salts, antibacterial agents, anti-tartar agents, breath reduction agents, chelants, structuring agents, TRPV1 or TRPA1 agonists, TRPV1 or TRPA1 antagonists, TRPM8 enhancers, flavor, tooth sensitivity actives, caries actives, abrasives, sorbitol, menthol, bitter blockers, anionic surfactant, cationic surfactant, nonionic surfactant, or combinations thereof is disclosed. Said composition can be used as an oral care composition.

In one aspect, said composition, is a cleaning and treatment composition.

In one aspect, said composition is a fabric and/or hard surface cleaning and/or treatment composition.

In one aspect, said composition is a detergent that comprises, based on total detergent weight, from about 0.00001% to about 25%, from 0.00005% to about 10%, from 0.0001% to about 5%, from 0.0005% to about 1.0%, or even from 0.001% to about 0.5% of one or more molecules according to Claim 1; and an adjunct ingredient.

In one aspect, said composition is highly compacted consumer product, said highly compacted consumer product that comprises, based on total highly compacted consumer product weight, from about 0.00001% to about 25%, from 0.00005% to about 10%, from 0.0001% to about 5%, from 0.0005% to about 1.0%, or even from 0.001% to about 0.5% of one or more molecules having a structure according to Structure 1 and/or Structure 2; and an adjunct ingredient.

In one aspect, said composition is highly compacted consumer product is a highly compacted detergent.

In one aspect, said composition comprises, based on total composition weight, from about 0.0001% to about 25%, from about 0.0005% to about 10%, from about 0.001% to about 5%, from about 0.005% to about 2.5%, or even from 0.01% to about 1% of one or more molecules having a structure according to Structure 1 and/or Structure 2; and an adjunct ingredient said composition being a consumer product.

Perfume Delivery Systems

In one aspect, a perfume delivery system comprising, based on total composition weight, at least 0.00001%, from about 0.001% to about 95%, from about 0.01% to about 85%, from about 0.01% to about 75%, from about 0.01% to about 65%, from about 0.01% to about 50%, from about 0.1% to about 15%, from about 0.1% to about 10% or even from about 0.5% to about 10% of one or more molecules having a structure according to Structure 1 and/or Structure 2 and an optional adjunct material, said perfume delivery system being a perfume delivery system selected from a polymer assisted delivery system; a molecule-assisted delivery system; a fiber-assisted delivery system; a cyclodextrin delivery system; a starch encapsulated accord; and/or an inorganic carrier delivery system is disclosed.

In one aspect, said perfume delivery system is a nanocapsule or a microcapsule comprising, based on total nanocapsule or microcapsule weight, at least 0.001%, from about 0.1% to about 99%, from 25% to about 95%, from 30 to about 90%, from 45% to about 90%, or from 65% to about 90% of one or more molecules having a structure according to Structure 1 and/or Structure 2.

In one aspect, said perfume delivery system being a starch encapsulated accord comprising, based on total starch encapsulate or starch agglomerate weight, at least 0.001%, from about 0.1% to about 99%, from 25% to about 95%, from 30 to about 90%, from 45% to about 90%, from 65% to about 90% of one or more molecules having a structure according to Structure 1 and/or Structure 2.

In one aspect, said perfume delivery system being a cyclodextrin delivery system comprising based on total cyclodextrin delivery system weight, at least 0.001%, from 0.1% to about 99%, from 2.5% to about 75%, from 5% to about 60%, from 5% to about 50%, from 5% to about 25% of one or more molecules having a structure according to Structure 1 and/or Structure 2.

In one aspect, said perfume delivery system being a polymer assisted delivery matrix system comprising, based on total polymer assisted delivery matrix system weight, at least 0.001%, from 0.1% to about 99%, from 2.5% to about 75%, from 5% to about 60%, from 5% to about 50%, from 5% to about 25% of one or more molecules having a structure according to Structure 1 and/or Structure 2.

In one aspect, a consumer product comprising, based on total consumer product weight, at least 0.001%, from about 0.001% to about 20%, from about 0.01% to about 10%, from about 0.05% to about 5%, from about 0.1% to about 0.5% of a perfume delivery system selected from the perfume delivery systems disclosed herein and mixtures thereof is disclosed.

Certain perfume delivery systems, methods of making certain perfume delivery systems and the uses of such perfume delivery systems are disclosed in USPA 2007/0275866 A1. Such perfume delivery systems include:

I. Polymer Assisted Delivery (PAD):

This perfume delivery technology uses polymeric materials to deliver perfume materials. Classical coacervation, water soluble or partly soluble to insoluble charged or neutral polymers, liquid crystals, hot melts, hydrogels, perfumed plastics, microcapsules, nano- and micro-latexes, polymeric film formers, and polymeric absorbents, polymeric adsorbents, etc. are some examples. PAD includes but is not limited to:

a.) Matrix Systems:

The fragrance is dissolved or dispersed in a polymer matrix or particle. Perfumes, for example, may be 1) dispersed into the polymer prior to formulating into the product or 2) added separately from the polymer during or after formulation of the product. Diffusion of perfume from the polymer is a common trigger that allows or increases the rate of perfume release from a polymeric matrix system that is deposited or applied to the desired surface (situs), although many other triggers are know that may control perfume release. Absorption and/or adsorption into or onto polymeric particles, films, solutions, and the like are aspects of this technology. Nano- or micro-particles composed of organic materials (e.g., latexes) are examples. Suitable particles include a wide range of materials including, but not limited to polyacetal, polyacrylate, polyacrylic, polyacrylonitrile, polyamide, polyaryletherketone, polybutadiene, polybutylene, polybutylene terephthalate, polychloroprene, poly ethylene, polyethylene terephthalate, polycyclohexylene dimethylene terephthalate, polycarbonate, polychloroprene, polyhydroxyalkanoate, polyketone, polyester, polyethylene, polyetherimide, polyethersulfone, polyethylenechlorinates, polyimide, polyisoprene, polylactic acid, polymethylpentene, polyphenylene oxide, polyphenylene sulfide, polyphthalamide, polypropylene, polystyrene, polysulfone, polyvinyl acetate, polyvinyl chloride, as well as polymers or copolymers based on acrylonitrile-butadiene, cellulose acetate, ethylene-vinyl acetate, ethylene vinyl alcohol, styrene-butadiene, vinyl acetate-ethylene, and mixtures thereof.

"Standard" systems refer to those that are "pre-loaded" with the intent of keeping the pre-loaded perfume associated with the polymer until the moment or moments of perfume release. Such polymers may also suppress the neat product odor and provide a bloom and/or longevity benefit depending on the rate of perfume release. One challenge with such systems is to achieve the ideal balance between 1) in-product stability (keeping perfume inside carrier until you need it) and 2) timely release (during use or from dry situs). Achieving such stability is particularly important during in-product storage and product aging. This challenge is particularly apparent for aqueous-based, surfactant-containing products, such as heavy duty liquid laundry detergents. Many "Standard" matrix systems available effectively become "Equilibrium" systems when formulated into aqueous-based products. One may select an "Equilibrium" system or a Reservoir system, which has acceptable in-product diffusion stability and available triggers for release (e.g., friction). "Equilibrium" systems are those in which the perfume and polymer may be added separately to the product, and the equilibrium interaction between perfume and polymer leads to a benefit at one or more consumer touch points (versus a free perfume control that has no polymer-assisted delivery technology). The polymer may also be pre-loaded with perfume; however, part or all of the perfume may diffuse during in-product storage reaching an equilibrium that includes having desired perfume raw materials (PRMs) associated with the polymer. The polymer then carries the perfume to the surface, and release is typically via perfume diffusion. The use of such equilibrium system polymers has the potential to decrease the neat product odor intensity of the neat product (usually more so in the case of pre-loaded standard system). Deposition of such polymers may serve to "flatten" the release profile and provide increased longevity. As indicated above, such longevity would be achieved by suppressing the initial intensity and may enable the formulator to use more high impact or low odor detection threshold (ODT) or low Kovats Index (KI) PRMs to achieve FMOT benefits without initial intensity that is too strong or distorted. It is important that perfume release occurs within the time frame of the application to impact the desired consumer touch point or touch points. Suitable microparticles and micro-latexes as well as methods of making same may be found in USPA 2005/0003980 A1. Matrix systems also include hot melt adhesives and perfume plastics. In addition, hydrophobically modified polysaccharides may be formulated into the perfumed product to increase perfume deposition and/or modify perfume release. All such matrix systems, including for example polysaccarides and nanolatexes may be combined with other PDTs, including other PAD systems such as PAD reservoir systems in the form of a perfume microcapsule (PMC). Polymer Assisted Delivery (PAD) matrix systems may include those described in US Patent Applications 2004/0110648 A1.

Silicones are also examples of polymers that may be used as PDT, and can provide perfume benefits in a manner similar to the polymer-assisted delivery "matrix system". Such a PDT is referred to as silicone-assisted delivery (SAD). One may pre-load silicones with perfume, or use them as an equilibrium system as described for PAD. Functionalized silicones may also be used. Examples of silicones include polydimethylsiloxane and polyalkyldimethylsiloxanes. Other examples include those with amine functionality, which may be used to provide benefits associated with amine-assisted delivery (AAD) and/or polymer-assisted delivery (PAD) and/or amine-reaction products (ARP).

b.) Reservoir Systems:

Reservoir systems are also known as a core-shell type technology, or one in which the fragrance is surrounded by a perfume release controlling membrane, which may serve as a protective shell. The material inside the microcapsule is referred to as the core, internal phase, or fill, whereas the wall is sometimes called a shell, coating, or membrane. Microparticles or pressure sensitive capsules or microcapsules are examples of this technology. Microcapsules of the current invention are formed by a variety of procedures that include, but are not limited to, coating, extrusion, spray-drying, interfacial, in-situ and matrix polymerization. The possible shell materials vary widely in their stability toward water. Among the most stable are polyoxymethyleneurea (PMU)-based materials, which may hold certain PRMs for even long periods of time in aqueous solution (or product). Such systems include but are not limited to urea-formaldehyde and/or melamine-formaldehyde. Stable shell materials include polyacrylate-based materials obtained as reaction product of an oil soluble or dispersible amine with a multifunctional acrylate or methacrylate monomer or oligomer, an oil soluble acid and an initiator, in presence of an anionic emulsifier comprising a water soluble or water dispersible acrylic acid alkyl acid copolymer, an alkali or alkali salt. Gelatin-based microcapsules may be prepared so that they dissolve quickly or slowly in water, depending for example on the degree of cross-linking. Many other capsule wall materials are available and vary in the degree of perfume diffusion stability observed. Without wishing to be bound by theory, the rate of release of perfume from a capsule, for example, once deposited on a surface is typically in reverse order of in-product perfume diffusion stability. As such, urea-formaldehyde and melamine-formaldehyde microcapsules for example, typically require a release mechanism other than, or in addition to, diffusion for release, such as mechanical force (e.g., friction, pressure, shear stress) that serves to break the capsule and increase the rate of perfume (fragrance) release. Other triggers include melting, dissolution, hydrolysis or other chemical reaction, electromagnetic radiation, and the like. The use of pre-loaded microcapsules requires the proper ratio of in-product stability and in-use and/or on-surface (on-situs) release, as well as proper selection of PRMs. Microcapsules that are based on urea-formaldehyde and/or melamine-formaldehyde are relatively stable, especially in near neutral aqueous-based solutions. These materials may require a friction trigger which may not be applicable to all product applications. Other microcapsule materials (e.g., gelatin) may be unstable in aqueous-based products and may even provide reduced benefit (versus free perfume control) when in-product aged. Scratch and sniff technologies are yet another example of PAD.

II. Molecule-Assisted Delivery (MAD):

Non-polymer materials or molecules may also serve to improve the delivery of perfume. Without wishing to be bound by theory, perfume may non-covalently interact with organic materials, resulting in altered deposition and/or release. Non-limiting examples of such organic materials include but are not limited to hydrophobic materials such as organic oils, waxes, mineral oils, petrolatum, fatty acids or esters, sugars, surfactants, liposomes and even other perfume raw material (perfume oils), as well as natural oils, including body and/or other soils. Perfume fixatives are yet another example. In one aspect, non-polymeric materials or molecules have a C Log P greater than about 2. Molecule-Assisted Delivery (MAD) may also include those described in U.S. Pat. No. 7,119,060.

III. Fiber-Assisted Delivery (FAD):

The choice or use of a situs itself may serve to improve the delivery of perfume. In fact, the situs itself may be a perfume delivery technology. For example, different fabric types such as cotton or polyester will have different properties with respect to ability to attract and/or retain and/or release perfume. The amount of perfume deposited on or in fibers may be altered by the choice of fiber, and also by the history or treatment of the fiber, as well as by any fiber coatings or treatments. Fibers may be woven and non-woven as well as natural or synthetic. Natural fibers include those produced by plants, animals, and geological processes, and include but are not limited to cellulose materials such as cotton, linen, hemp jute, flax, ramie, and sisal, and fibers used to manufacture paper and cloth. Fiber-Assisted Delivery may consist of the use of wood fiber, such as thermomechanical pulp and bleached or unbleached kraft or sulfite pulps. Animal fibers consist largely of particular proteins, such as silk, sinew, catgut and hair (including wool). Polymer fibers based on synthetic chemicals include but are not limited to polyamide nylon, PET or PBT polyester, phenol-formaldehyde (PF), polyvinyl alcohol fiber (PVOH), polyvinyl chloride fiber (PVC), polyolefins (PP and PE), and acrylic polymers. All such fibers may be pre-loaded with a perfume, and then added to a product that may or may not contain free perfume and/or one or more perfume delivery technologies. In one aspect, the fibers may be added to a product prior to being loaded with a perfume, and then loaded with a perfume by adding a perfume that may diffuse into the fiber, to the product. Without wishing to be bound by theory, the perfume may absorb onto or be adsorbed into the fiber, for example, during product storage, and then be released at one or more moments of truth or consumer touch points.

IV. Cyclodextrin Delivery System (CD):

This technology approach uses a cyclic oligosaccharide or cyclodextrin to improve the delivery of perfume. Typically a perfume and cyclodextrin (CD) complex is formed. Such complexes may be preformed, formed in-situ, or formed on or in the situs. Without wishing to be bound by theory, loss of water may serve to shift the equilibrium toward the CD-Perfume complex, especially if other adjunct ingredients (e.g., surfactant) are not present at high concentration to compete with the perfume for the cyclodextrin cavity. A bloom benefit may be achieved if water exposure or an increase in moisture content occurs at a later time point. In addition, cyclodextrin allows the perfume formulator increased flexibility in selection of PRMs. Cyclodextrin may be pre-loaded with perfume or added separately from perfume to obtain the desired perfume stability, deposition or release benefit. Suitable CDs as well as methods of making same may be found in USPA 2005/0003980 A1.

V. Starch Encapsulated Accord (SEA):

The use of a starch encapsulated accord (SEA) technology allows one to modify the properties of the perfume, for example, by converting a liquid perfume into a solid by adding ingredients such as starch. The benefit includes increased perfume retention during product storage, especially under non-aqueous conditions. Upon exposure to moisture, a perfume bloom may be triggered. Benefits at other moments of truth may also be achieved because the starch allows the product formulator to select PRMs or PRM concentrations that normally cannot be used without the presence of SEA. Another technology example includes the use of other organic and inorganic materials, such as silica to convert perfume from liquid to solid. Suitable SEAs as well as methods of making same may be found in U.S. Pat. No. 6,458,754 B1.

VI. Inorganic Carrier Delivery System (ZIC):

This technology relates to the use of porous zeolites or other inorganic materials to deliver perfumes. Perfume-loaded zeolite may be used with or without adjunct ingredients used for example to coat the perfume-loaded zeolite (PLZ) to change its perfume release properties during product storage or during use or from the dry situs. Suitable zeolite and inorganic carriers as well as methods of making same may be found in USPA 2005/0003980 A1. Silica is another form of ZIC. Another example of a suitable inorganic carrier includes inorganic tubules, where the perfume or other active material is contained within the lumen of the nano- or micro-tubules. In one aspect, the perfume-loaded inorganic tubule (or Perfume-Loaded Tubule or PLT) is a mineral nano- or micro-tubule, such as halloysite or mixtures of halloysite with other inorganic materials, including other clays. The PLT technology may also comprise additional ingredients on the inside and/or outside of the tubule for the purpose of improving in-product diffusion stability, deposition on the desired situs or for controlling the release rate of the loaded perfume. Monomeric and/or polymeric materials, including starch encapsulation, may be used to coat, plug, cap, or otherwise encapsulate the PLT. Suitable PLT systems as well as methods of making same may be found in U.S. Pat. No. 5,651,976.

In another aspect, the perfume delivery systems disclosed herein are suitable for use in consumer products, cleaning and treatment compositions, fabric and hard surface cleaning and/or treatment compositions, detergents, and highly compacted consumer products, including highly compacted fabric and hard surface cleaning and/or treatment compositions (e.g., solid or fluid highly compacted detergents) at levels, based on total consumer product weight, from about 0.001% to about 20%, from about 0.01% to about 10%, from about 0.05% to about 5%, from about 0.1% to about 0.5%.

The perfume delivery technologies (a.k.a., perfume delivery systems) that are disclosed in the present specification may be used in any combination in any type of consumer product, cleaning and/or treatment composition, fabric and hard surface cleaning and/or treatment composition, detergent, and/or highly compact detergent.

Perfumes

The molecules having a structure according to Structure 1 and/or Structure 2 may be used to formulate perfumes. Such perfumes are combinations of molecules that may be employed, based on total perfume weight, at levels of from about 0.01% to about 50%, from about 0.1% to about 15%, from about 0.1% to about 10% or even from about 0.5% to about 10%. Such perfumes may be utilized in various applications, including being applied neat to a situs or used in a consumer product, cleaning and/or treatment composition, fabric and hard surface cleaning and/or treatment composition, detergent, and/or a highly compact detergent.

Adjunct Materials

For the purposes of the present invention, the non-limiting list of adjuncts illustrated hereinafter are suitable for use in the compositions detailed herein (e.g., consumer products, cleaning and/or treatment compositions, fabric and hard surface cleaning and/or treatment compositions, detergents, and/or a highly compact detergents). Such adjunct materials may be desirably incorporated in certain embodiments of the compositions, for example to assist or enhance performance of the composition, for treatment of the substrate to be cleaned, or to modify the aesthetics of the composition as is the case with perfumes, colorants, dyes or the like. It is understood that such adjuncts are in addition to the components that are supplied via Applicants' perfumes and/or perfume systems detailed herein. The precise nature of these additional components, and levels of incorporation thereof, will depend on the physical form of the composition and the nature of the operation for which it is to be used.

Suitable adjunct materials include, but are not limited to, surfactants, builders, chelating agents, dye transfer inhibiting agents, dispersants, enzymes, and enzyme stabilizers, catalytic materials, bleach activators, polymeric dispersing agents, clay soil removal/anti-redeposition agents, brighteners, suds suppressors, dyes, additional perfume and perfume delivery systems, structure elasticizing agents, fabric softeners, carriers, hydrotropes, processing aids and/or pigments, metal salts, structurants or binders, anti-tartar agents, anti-caries agents, abrasives, fillers, humectants, breath agents, flavors, antibacterial agents. In addition to the disclosure below, suitable examples of such other adjuncts and levels of use are found in U.S. Pat. No. 6,326,348 B1.

Each adjunct ingredient is not essential to Applicants' compositions. Thus, certain embodiments of Applicants' compositions may not contain one or more of the following adjuncts materials: bleach activators, surfactants, builders, chelating agents, dye transfer inhibiting agents, dispersants, enzymes, and enzyme stabilizers, catalytic metal complexes, polymeric dispersing agents, clay and soil removal/anti-redeposition agents, brighteners, suds suppressors, dyes, additional perfumes and perfume delivery systems, structure elasticizing agents, fabric softeners, carriers, hydrotropes, processing aids and/or pigments, metal salts, structurants or binders, anti-tartar agents, anti-caries agents, abrasives, fillers, humectants, breath agents, flavors, antibacterial agents. However, when one or more adjuncts are present, such adjuncts may be present as detailed below:

Surfactants—The compositions according to the present invention can comprise a surfactant or surfactant system wherein the surfactant can be selected from nonionic and/or anionic and/or cationic surfactants and/or ampholytic and/or zwitterionic and/or semi-polar nonionic surfactants. The surfactant is typically present at a level of from about 0.1%, from about 1%, or even from about 5% by weight of the cleaning compositions to about 99.9%, to about 80%, to about 35%, or even to about 30% by weight of the cleaning compositions.

Builders—The compositions of the present invention can comprise one or more detergent builders or builder systems. When present, the compositions will typically comprise at least about 1% builder, or from about 5% or 10% to about 80%, 50%, or even 30% by weight, of said builder. Builders include, but are not limited to, the alkali metal, ammonium and alkanolammonium salts of polyphosphates, alkali metal silicates, alkaline earth and alkali metal carbonates, aluminosilicate builders polycarboxylate compounds. ether hydroxypolycarboxylates, copolymers of maleic anhydride with ethylene or vinyl methyl ether, 1,3,5-trihydroxybenzene-2,4,6-trisulphonic acid, and carboxymethyl-oxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Chelating Agents—The compositions herein may also optionally contain one or more copper, iron and/or manganese chelating agents. If utilized, chelating agents will generally comprise from about 0.1% by weight of the compositions herein to about 15%, or even from about 3.0% to about 15% by weight of the compositions herein.

Dye Transfer Inhibiting Agents—The compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in the compositions herein, the dye transfer inhibiting agents are present at levels from about 0.0001%, from about 0.01%, from about 0.05% by weight of the cleaning compositions to about 10%, about 2%, or even about 1% by weight of the cleaning compositions.

Dispersants—The compositions of the present invention can also contain dispersants. Suitable water-soluble organic materials are the homo- or co-polymeric acids or their salts, in which the polycarboxylic acid may comprise at least two carboxyl radicals separated from each other by not more than two carbon atoms.

Enzymes—The compositions can comprise one or more detergent enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. A typical combination is a cocktail of conventional applicable enzymes like protease, lipase, cutinase and/or cellulase in conjunction with amylase.

Enzyme Stabilizers—Enzymes for use in compositions, for example, detergents can be stabilized by various techniques. The enzymes employed herein can be stabilized by the presence of water-soluble sources of calcium and/or magnesium ions in the finished compositions that provide such ions to the enzymes.

Catalytic Metal Complexes—Applicants' compositions may include catalytic metal complexes. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra(methyl-enephosphonic acid) and water-soluble salts thereof. Such catalysts are disclosed in U.S. Pat. No. 4,430,243.

If desired, the compositions herein can be catalyzed by means of a manganese compound. Such compounds and levels of use are well known in the art and include, for example, the manganese-based catalysts disclosed in U.S. Pat. No. 5,576,282. Cobalt bleach catalysts useful herein are known, and are described, for example, in U.S. Pat. No. 5,597,936.

Compositions herein may also suitably include a transition metal complex of a macropolycyclic rigid ligand—abbreviated as "MRL". As a practical matter, and not by way of limitation, the compositions and cleaning processes herein can be adjusted to provide on the order of at least one part per hundred million of the benefit agent MRL species in the aqueous washing medium, and may provide from about 0.005 ppm to about 25 ppm, from about 0.05 ppm to about 10 ppm, or even from about 0.1 ppm to about 5 ppm, of the MRL in the wash liquor. Suitable transition-metals in the instant transition-metal bleach catalyst include manganese, iron and chromium. Suitable MRL's herein are a special type of ultra-rigid ligand that is cross-bridged such as 5,12-diethyl-1,5,8,12-tetraazabicyclo[6.6.2]hexa-decane. Suitable transition metal MRLs are readily prepared by known procedures, such as taught for example in and U.S. Pat. No. 6,225,464.

Methods of Use

Some of the consumer products disclosed herein can be used to clean or treat a situs inter alia a surface or fabric. Typically at least a portion of the situs is contacted with an embodiment of Applicants' composition, in neat form or diluted in a liquor, for example, a wash liquor and then the situs may be optionally washed and/or rinsed. In one aspect, a situs is optionally washed and/or rinsed, contacted with a composition according to the present invention and then optionally washed and/or rinsed. The situs may also then be dried via line drying and/or machine drying. For purposes of the present invention, washing includes but is not limited to, scrubbing, and mechanical agitation. The fabric may comprise most any fabric capable of being laundered or treated in normal consumer use conditions. Liquors that may comprise the disclosed compositions may have a pH of from about 3 to about 11.5. Such compositions are typically employed at concentrations of from about 500 ppm to about 15,000 ppm in solution. When the wash solvent is water, the water temperature typically ranges from about 5° C. to about 90° C. and, when the situs comprises a fabric, the water to fabric ratio is typically from about 1:1 to about 30:1.

Test Methods

It is understood that the test methods that are disclosed in the Test Methods Section of the present application should be used to determine the respective values of the parameters of Applicants' invention as such invention is described and claimed herein.

(1) C log P

The log P values of many perfume ingredients have been reported; for example, the Pomona92 database, available from Daylight Chemical Information Systems, Inc. (Daylight CIS), Irvine, Calif., contains many, along with citations to the original literature. However, the log P values are most conveniently calculated by the "C LOG P" program, also available from Daylight CIS. This program also lists experimental log P values when they are available in the Pomona92 database. The "calculated log P" (C log P) is determined by the fragment approach of Hansch and Leo (cf., A. Leo, in Comprehensive Medicinal Chemistry, Vol. 4, C. Hansch, P. G. Sammens, J. B. Taylor and C. A. Ramsden, Eds., p. 295, Pergamon Press, 1990, incorporated herein by reference). The fragment approach is based on the chemical structure of each perfume ingredient, and takes into account the numbers and types of atoms, the atom connectivity, and chemical bonding. The C log P values, which are the most reliable and widely used estimates for this physicochemical property, are preferably used instead of the experimental log P values in the selection of perfume ingredients which are useful in the present invention.

(2) Boiling Point

Boiling point is measured by ASTM method D2887-04a, "Standard Test Method for Boiling Range Distribution of Petroleum Fractions by Gas Chromatography," ASTM International.

(3) Headspace Ratio (a) Obtain a fragrance free consumer product formulation.

(b) Obtain fragrance microcapsules whose water content has been adjusted to achieve a perfume content of 25 wt % in the aqueous slurry.

(c) Prepare Sample A by adding 2.0 grams of the fragrance microcapsule aqueous slurry to 95 grams of the fragrance free consumer product formulation. Then add 3.0 grams of deionized water to balance the formulation to 100 grams. Age this formulation for 1 week at 40 degrees Centigrade.

(d) Prepare Sample B by adding 0.50 grams of the neat fragrance to 95 grams of fragrance free consumer product formulation. Then add 4.5 grams of deionized water to balance the formulation to 100 grams. Age this formulation for 1 week at 40 degrees Centigrade.

The Headspace Ratio for determining perfume leakage from a perfume delivery system is defined as the headspace concentration of Sample A divided by the headspace concentration of Sample B, $$\frac{H_{Sample\_A}}{H_{Sample\_B}},$$

where $H_{Sample\_A}$ is the headspace concentration of a consumer product formulation Sample A, and $H_{Sample\_B}$ is the headspace concentration of a consumer product formulation Sample B.

The Headspace Ratio for determining perfume delivery efficiency from a perfume delivery system is defined as the headspace concentration of Sample B divided by the headspace concentration of Sample A, $$\frac{H_{Sample\_B}}{H_{Sample\_A}},$$

where $H_{Sample\_A}$ is the headspace concentration of a consumer product formulation Sample A, and $H_{Sample\_B}$ is the headspace concentration of a consumer product formulation Sample B.

Solid-Phase Micro-Extraction (SPME)-Gas Chromatography/Mass Spectrometry is used to measure the level of perfume raw materials in the headspace of products. 1.0 grams of the 1 week at 40 degrees Centigrade aged sample are placed into a clean 20 ml headspace vial and allowed to equilibrate for at least 2 hours at room temperature.

The samples are then analyzed using the MPS2-SMPE-GC-MS analysis system (GC-02001-0153, MSD-02001-0154, MPS2-02001-0155).

Apparatus:

1. 20 ml headspace vial
2. Timer.
3. Gas Chromatograph (GC): Agilent model 6890 with a CIS-4 injector (Gerstel, Mulheim, Germany) and MPS-2 Autosampler and TDU. For SPME analysis, we used the split/splitless injector (not the CIS-4 injector).
4. GC column: J&W DB-5 MS, 30 M×0.25 mm ID, 1.0 m film thickness obtained from J&W Scientific of Folsom, Calif., USA.
5. Carrier gas, helium, 1.5 ml/min. flow rate.
6. The injector liner is a special SPME liner (0.75 mm ID) from Supelco.
7. The Detector is a model 5973 Mass Selective Detector obtained from Agilent Technologies, Inc., Wilmington, Del., USA having a source temperature of about 230° C., and a MS Quad temperature of about 150° C.

Analysis Procedure:
1. Transfer sample to proper sample tray and proceed with SPME-GC-MS analysis.
2. Start sequence of sample loading and analysis. In this step, the sample is allowed to equilibrate for at least two hours on the auto sampler tray, then sampled directly from the tray. The SPME fiber assembly is DVB/CAR/PDMS (50/30 um, 24 ga, 1 cm length). Sampling time is 5 minutes.
3. Injector temperature is at 260 C.
4. Then GC-MS analysis run is started. Desorption time is 5 minutes.
5. The following temperature program is used:
   i) an initial temperature of about 50° C. which is held for 3 minutes,
   ii) increase the initial temperature at a rate of about 6° C./min until a temperature of about 250° C. is reached, then 25° C./min to 275° C., hold at about 275° C. for 4.67 minute.
6. Perfume compounds are identified using the MS spectral libraries of John Wiley & Sons and the National Institute of Standards and Technology (NIST), purchased and licensed through Hewlett Packard.
7. Chromatographic peaks for specific ions are integrated using the Chemstation software obtained from Agilent Technologies, Inc., Wilmington, Del., USA.
8. The ratio for each PRM is calculated by dividing the peak area for the perfume raw material in Sample A by the peak area in Sample B.
9. Each ratio is then weighted by that perfume raw material's weight composition in the perfume.
10. The Headspace Ratio is calculated as the sum of the individual perfume raw material ratios obtained in step 9.

(4) Perfume Leakage can Also be Evaluated Via % Liquid-Liquid Extraction and Gas Chromatographic-Mass Spectrometric Analysis When determining the % perfume leakage from Perfume Microcapsules in liquid detergent, a fresh sample of liquid detergent with equal level of free perfume (without Perfume Microcapsules) must also be analyzed in parallel for reference.

1. Preparation of an Internal Standard Solution
   Stock solution of tonalid: Weigh 70 mg tonalid and add 20 ml hexane p.a.
   Internal Standard Solution solution: Dilute 200 µl of stock solution in 20 ml hexane p.a.
   Mix to homogenize 2. Perfume Extraction from Liquid Detergent without Perfume Microcapsules (Reference)
   Weigh 2 g of liquid detergent product into an extraction vessel
   Add 2 ml of Internal Standard Solution and close vessel
   Extract perfume by gently turning the extraction vessel upside-down for 20 times (manually)
   Add spoon tip of Sodium Sulphate
   After separation of layers, immediately transfer hexane-layer into Gas Chromatograph auto sampler-vial and cap vial
   Inject splitless (1.5 µl) into Gas Chromatograph injection-port
   Run Gas Chromatographic-Mass Spectrometric analysis 3. Perfume Extraction from Liquid Detergent with Perfume Microcapsules
   Weigh 2 g of liquid detergent product into an extraction vessel
   Add 2 ml of Internal Standard Solution and close vessel
   Extract perfume by gently turning the extraction vessel upside-down for 20 times (manually)
   Add spoon tip of Sodium Sulphate
   After separation of layers, immediately transfer hexane-layer into Gas Chromatograph auto sampler-vial and cap vial
   Inject splitless (1.5 µl) into Gas Chromatograph injection-port
   Run Gas Chromatographic-Mass Spectrometric analysis 4. Calculation
   The perfume leakage from capsules per individual Perfume Raw Material:

% perfume leakage=((Area Perfume Raw Material caps×Area Internal Standard Solution ref×Weight ref)/(Area Internal Standard Solution caps×Area Perfume Raw Material ref×Weight caps))×100

(5) Odor Detection Threshold (ODT)

Determined using a gas chromatograph. The gas chromatograph is calibrated to determine the exact volume of material injected by the syringe, the precise split ratio, and the hydrocarbon response using a hydrocarbon standard of known concentration and chain length distribution. The air flow rate is accurately measured and, assuming the duration of human inhalation to last 12 seconds, the sampled volume is calculated. Since the precise concentration at the detector at any point in time is known, the mass per volume inhaled is known, and hence the concentration of material.

For example, to determine whether a material has a threshold below 50 parts per billion, solutions are delivered to the sniff port at the calculated concentration. A panelist sniffs the GC effluent and identifies the retention time when odor is noticed. The average among 6 panelists determines the threshold of notice ability. The necessary amount of analyte is injected into the column to achieve a 50 parts per billion concentration at the detector. Typical gas chromatograph parameters for determining odor detection thresholds are listed below:
   GC: 5890 Series II with FID detector, 7673 Autosampler
   Column: J&W Scientific DB-1
   Length: 30 meters, 0.25 millimeter inside diameter, 1 micrometer film thickness
   Method:
   split injection: 17/1 split ratio
   Autosampler: 1.13 microliters per injection
   Column flow: 1.10 milliLiters per minute
   Air Flow: 345 milliLiters per minute
   Inlet Temperature: 245 degrees Centigrade
   Detector Temperature: 285 degrees Centigrade
   Initial Temperature=50 degrees Centigrade, 5 degrees Centigrade per minute ramp rate, final temperature=280 degrees Centigrade, Final time=6 minutes
   Leading assumptions: 12 seconds per sniff, GC air adds to sample dilution (6) Coolant Screening on the TRPM8 Receptor HEK-23 (human embryonic kidney) cells stably transfected with human TRPM8 were grown in 15 ml growth medium [high glucose DMEM (Dulbecco's Modification of Eagle's Medium) supplemented with 10% FBS (fetal bovine serum), 100 ug/ml Penicillin/streptomycin, 5 µg/ml blasticindin, and 100 µg/ml zeocin) in a 75 CM 2 flask for 3 days at 37° C. in a mammalian cell culture incubator set at 5% CO2. Cells were detached with addition of 2 ml of trypsin-EDTA buffer (GIBCO® 25200, Invitrogen) for about 2-3 min. Trypsin was inactivated by addition of 8 ml growth medium. Cells were transferred to a 50 ml tube and centrifuged at 850 rpm for 3 minutes to remove medium. After centrifugation, a pellet of cells was formed in the bottom of the tube separating them from the supernatant solution. The supernatant was discarded and the cell pellet was suspended in 1 ml of fresh growth medium to which 5 ul (12.5 ug) of Fluo-4 AM (Molecular Probes, Inc.) calcium indicator was added and incubated for 30 min with gentle shaking. (Fluo-4 is a fluorescent dye used for quantifying cellular Ca t concentrations in the 100 nM to 1 microM range.) At the end of 30 minutes, 45 ml of assay buffer [1×HBSS (Hank's Balanced Salt Solution), 20 mM HEPES (4-(2-Hydroxyethyl)-1-piperazineethanesulfonic acid)] was added to wash cells and the resulting mixture was then centrifuged at 850 rpm for 3 minutes to remove excess buffer and Fluo-4 AM calcium indicator. The pellet cells were re-suspended in 10 ml assay buffer and 90 ul aliquots (~50,000 cells) per well delivered to a 96-well assay plate containing 10 ul of test compounds (1 mM in assay buffer, final concentration 100 uM) or buffer control and incubated at room temperature for 30 minutes. After 30 minutes, plate is placed into a fluorometric imaging plate reader (FLIPR 384 from Molecular Devices) and basal fluorescence recorded (excitation wave length 488 nm and emission wave length 510 nm). The FLIPR assay is an accepted method for detecting changes in intracellular calcium concentration. Then 20 ul of 37.5 uM of the compounds of the invention were tested as TRPM8 agonist in the assay buffer (final concentration 6.25 uM) was added and fluorescence recorded. For determining the direct effect of test compounds on TRPM8, fluorescence was measured immediately after addition of each compound.

EXAMPLES

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

Example 1

PRM Synthesis

| | Chemical Structure-6 member ring variant | IUPAC Names | Chemical Structure-7 member ring variant | IUPAC Names |
|---|---|---|---|---|
| 1 | | (R,S)-3-isobutyl-1,4,6-trimethyl-2-oxabicyclo[2.2.2]octane | | (R,S)-7-isobutyl-1,4,5-trimethyl-6-oxabicyclo[3.2.1]octane |
| 2 | | (R,S)-3-butyl-4-ethyl-1,6-dime-thyl-2-oxabicyclo[2.2.2]octane | | (R,S)-7-butyl-1-ethyl-4,5-dimethyl-6-oxabicyclo[3.2.1]octane |
| 3 | | (R,S)-1,3,4,6-tetramethyl-2-oxabicyclo[2.2.2]octane | | (R,S)-1,4,5,7-tetramethyl-6-oxabicyclo[3.2.1]octane |
| 4 | | (R,S)-4-ethyl-1,3,6-trimethyl-2-oxabicyclo[2.2.2]octane | | (R,S)-1-ethyl-4,5,7-trimethyl-6-oxabicyclo[3.2.1]octane |

-continued

| | Chemical Structure-6 member ring variant | IUPAC Names | Chemical Structure-7 member ring variant | IUPAC Names |
|---|---|---|---|---|
| 5 | | (R,S)-4-isopropyl-1,6-dimethyl-2-oxa-bicyclo[2.2.2]octane | | (R,S)-1-isopropyl-4,5-dimethyl-6-oxabicyclo[3.2.1]octane |
| 6 | | 1,6-dimethyl-4-(R,S)-propyl-2-oxa-bicyclo[2.2.2]octane | | (R,S)-4,5-dimethyl-1-propyl-6-oxabicyclo[3.2.1]octane |
| 7 | | 4-(R,S)-allyl-1,6-dimethyl-2-oxa-bicyclo[2.2.2]octane | | (R,S)-1-allyl-4,5-dimethyl-6-oxabicyclo[3.2.1]octane |
| 8 | | (R,S)-1,4,6-trimethyl-2-oxa-bicyclo[2.2.2]octane | | (R,S)-1,4,5-trimethyl-6-oxabicyclo[3.2.1]octane |
| 9 | | (R,S)-1,3,3,4,6-pentamethyl-2-oxa-bicyclo[2.2.2]octane | | (R,S)-1,4,5,7,7-pentamethyl-6-oxabicyclo[3.2.1]octane |
| 10 | | (R,S)-4-ethyl-1,6-dimethyl-2-oxa-bicyclo[2.2.2]octane | | (R,S)-1-ethyl-4,5-dimethyl-6-oxabicyclo[3.2.1]octane |
| 11 | | 1,3,6-trimethyl-4-propyl-2-oxabicyclo[2.2.2]octane | | (R,S)-4,5,7-trimethyl-1-propyl-6-oxabicyclo[3.2.1]octane |

| Chemical Structure-6 member ring variant | IUPAC Names | Chemical Structure-7 member ring variant | IUPAC Names |
|---|---|---|---|
| 12 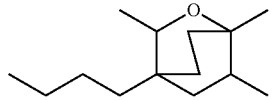 | 4-butyl-1,3,6-trimethyl-2-oxabicyclo[2.2.2]octane | 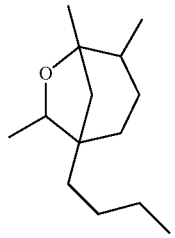 | (R,S)-1-butyl-4,5,7-trimethyl-6-oxabicyclo[3.2.1]octane |
| 13 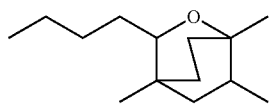 | 3-butyl-1,4,6-trimethyl-2-oxabicyclo[2.2.2]octane | 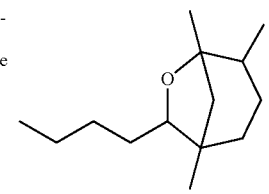 | (R,S)-7-butyl-1,4,5-trimethyl-6-oxabicyclo[3.2.1]octane |

Example 1

Synthesis of Table 1 Molecules

Synthesis of 3,4-dimethylcyclohex-3-enecarbonitrile

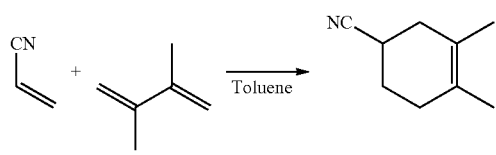

A solution of acrylonitrile (1 eq.) and 2,3-dimethylbuta-1,3-diene (1.1 eq.) in toluene (2M) was pumped through a heated coil reactor at 240° C. with a residence time of 10 minutes. The resulting mixture was concentrated under reduced pressure and yielded the product as colorless oil (87% yield).

Synthesis of methyl 3,4-dimethylcyclohex-3-enecarboxylate

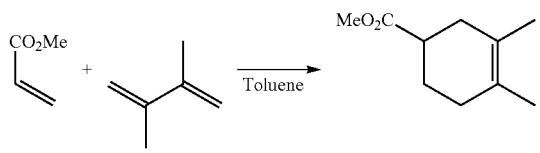

A solution of methyl acrylate (1 eq.) and 2,3-dimethylbuta-1,3-diene (1.1 eq.) in toluene (2M) was pumped through a heated coil reactor at 220° C. with a residence time of 17 minutes. The resulting mixture was concentrated under reduced pressure and yielded the product as colorless oil (87% yield).

Synthesis of intermediates, alkylations 3,4-dimethylcyclohex-3-enecarbonitrile or methyl 3,4-dimethylcyclohex-3-enecarboxylate

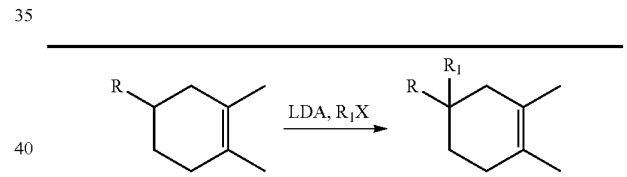

| —R | $R_1$ | Intermediate for compound # Table 1 | X |
|---|---|---|---|
| —CN | methyl | 1, 3 & 13 | I |
| —CN | ethyl | 2 & 4 | Br |
| —CN | n-propyl | 11 | I |
| —CN | n-butyl | 12 | I |
| —$CO_2Me$ | methyl | 8 & 9 | I |
| —$CO_2Me$ | ethyl | 10 | Br |
| —$CO_2Me$ | iso-propyl | 5 | I |
| —$CO_2Me$ | n-propyl | 6 | I |
| —$CO_2Me$ | allyl | 7 | Br |

A representative procedure for the methylation of 3,4-dimethylcyclohex-3-enecarbonitrile:

To a solution of di-isopropylamine (1.05 eq.) in dry THF (0.5 M) at 0° C., was added drop wise a solution of n-butyllithium (1.05 eq.-2.2 M cyclohexane). After stirring for 10 minutes at the same temperature, 3,4-dimethylcyclohex-3-enecarbonitrile (1 eq.) was added drop wise to this mixture. After another 10 minutes, iodomethane was added drop wise at 0° C. Complete conversion was observed after 10 minutes stirring. The reaction was quenched by addition of a saturated $NH_4Cl$ aqueous solution and extracted with $Et_2O$. The combined organic layers were dried over $MgSO_4$ and concentrated under reduced pressure. The resulting oil was purified using a quick filtration over silica by elution with a petroleum ether-Et$_2$O mixture (9-1). Concentration of the eluent under reduced pressure resulted in the compound as a colorless oil (92% yield).

Synthesis of Intermediates, Nitrile Alkylations

| R$_1$ | R$_2$ | Intermediate for compound # Table 1 |
|---|---|---|
| methyl | iso-butyl | 1 |
| ethyl | n-butyl | 2 |
| methyl | n-butyl | 13 |
| methyl | methyl | 3 |
| ethyl | methyl | 4 |
| n-propyl | methyl | 11 |
| n-butyl | methyl | 12 |

A representative procedure is given for the synthesis of intermediate for compound 3.

A methyllithium solution (1.2 equiv.) was added drop wise to a solution of the nitrile (1 eq.) in dry THF (0.5M) at −20° C. After stirring for 15 minutes at −10/−20° C., full conversion was observed by GC-MS. The reaction was quenched with a H$_2$SO$_4$ solution (2M-2 eq.) and stirred at ambient temperature till full hydrolysis of the in situ formed imine was observed. The mixture was then extracted with Et$_2$O and washed with a saturated NaHCO$_3$ aqueous solution. The combined organic phases were dried over MgSO$_4$ and concentrated under reduced pressure. The resulting oil was purified using a quick filtration over silica gel by eluting with a petroleum ether-Et$_2$O mixture (9-1). Concentration of the eluent under reduced pressure resulted in the compound as a colorless oil (89% yield).

Synthesis of Intermediates, Reduction of Ketones/Methyl Esters

| R$_1$ | R$_2$ | Intermediate for compound # Table 1 |
|---|---|---|
| methyl | iso-butyl | 1 |
| ethyl | n-butyl | 2 |
| methyl | methyl | 3 |
| ethyl | methyl | 4 |
| iso-propyl | —OMe | 5 |
| n-propyl | —OMe | 6 |
| allyl | —OMe | 7 |
| methyl | —OMe | 8 |
| ethyl | —OMe | 10 |
| n-propyl | methyl | 11 |
| n-butyl | methyl | 12 |
| methyl | n-butyl | 13 |

A representative procedure is given for the synthesis of intermediate for compound 1.

To a solution of ketone (1 eq.) in dry THF (0.5 M) was added portion wise lithium-aluminiumhydride (0.5 eq.) at 0° C. Reaction completion was observed by GC-MS after 15 minutes of stirring at ambient temperature. The mixture was cooled to 0° C. and consequently was added: water (same amount of mL as mg hydride used), 15% NaOH solution (same amount of mL as mg hydride used) & water (2 times amount of mL as mg hydride used). This quenching was followed by stirring for 1 hour at ambient temperature. The resulting mixture was filtered over celite and the filter was washed with Et$_2$O. Concentration of the filtrate under reduced pressure resulted in the compound as a colorless oil (94% yield).

Synthesis of intermediate, 2-(1,3,4-trimethylcyclohex-3-en-1-yl)propan-2-ol

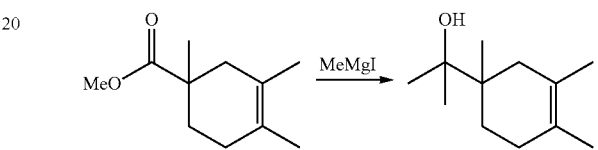

To a solution of methyl 1,3,4-trimethylcyclohex-3-enecarboxylate (1 eq.) in dry THF (0.5 M) at −20° C. was added drop wise a solution of methylmagnesium iodide (2.1 eq.-3 M). The resulting mixture was stirred overnight at ambient temperature and successively quenched with a saturated NH$_4$Cl solution and extracted with Et$_2$O. The combined organic layers were dried over MgSO$_4$ and concentrated under reduced pressure. The resulting oil was purified using a quick filtration over silica by elution with a petroleum ether-Et$_2$O mixture (1-1). Concentration of the eluent under reduced pressure resulted in the compound as a colorless oil (86% yield).

Synthesis of compounds 1-10 Table 1

| R$_1$ | R$_2$ | R$_3$ | Intermediate for compound # Table 1 |
|---|---|---|---|
| methyl | iso-butyl | H | 1 |
| ethyl | n-butyl | H | 2 |
| methyl | methyl | H | 3 |
| ethyl | methyl | H | 4 |
| iso-propyl | H | H | 5 |
| n-propyl | H | H | 6 |
| allyl | H | H | 7 |

| | | | |
|---|---|---|---|
| methyl | H | H | 8 |
| methyl | methyl | methyl | 9 |
| ethyl | H | H | 10 |
| n-propyl | methyl | H | 11 |
| n-butyl | methyl | H | 12 |
| methyl | n-butyl | H | 13 |

A representative procedure is given for the synthesis of intermediate for compound 3 Table 1.

A mixture of 1-(1,3,4-trimethylcyclohex-3-en-1-yl)ethanol (1 eq.) and Cu(OTf)$_2$ (3 mol %) in toluene is stirred overnight at 65° C. The resulting mixture is concentrated under reduced pressure and purified using a quick filtration over silica by elution with a petroleum ether-Et$_2$O mixture (9-1). Concentration of the eluent under reduced pressure resulted in the compound as a colorless oil (65% yield).

Example 2

84 wt % Core/16 wt % Wall Melamine Formaldehyde (MF) Capsule (PAD Reservoir System 17 grams of butyl acrylate-acrylic acid copolymer emulsifier (Colloid C351, 25% solids, pka 4.5-4.7, (Kemira Chemicals, Inc. Kennesaw, Ga. U.S.A.) and 17 grams of polyacrylic acid (35% solids, pKa 1.5-2.5, Aldrich) are dissolved and mixed in 200 grams deionized water. The pH of the solution is adjusted to pH of 6.0 with sodium hydroxide solution. 7 grams of partially methylated methylol melamine resin (Cymel 385, 80% solids, (Cytec Industries West Paterson, N.J., U.S.A.)) is added to the emulsifier solution. 200 grams of perfume oil is added to the previous mixture under mechanical agitation and the temperature is raised to 45° C. After mixing at higher speed until a stable emulsion is obtained, the second solution and 4 grams of sodium sulfate salt are added to the emulsion. This second solution contains 3 grams of polyacrylic acid polymer (Colloid C121, 25% solids (Kemira Chemicals, Inc. Kennesaw, Ga. U.S.A.), 100 grams of distilled water, sodium hydroxide solution to adjust pH to 6.0, 10 grams of partially methylated methylol melamine resin (Cymel 385, 80% Cytec). This mixture is heated till 85 C and maintained 8 hours with continuous stirring to complete the encapsulation process. 23 grams of acetoacetamide (Sigma-Aldrich, Saint Louis, Mo. U.S.A.) is added to the suspension. Salts and structuring agents can then still be added to the slurry.

Example 3

Process of Making a Polymer Assisted Delivery (PAD) Matrix System

A mixture comprising 50% of a perfume composition comprising one or more Table 1 PRMs, 40% of carboxyl-terminated Hypro™ RLP 1300×18 (CAS#0068891-50-9) from nanoresins, (put at 60° C. in warm water bath for 1 hour before mixing) and 10% of Lupasol® WF (CAS#09002-98-6) from BASF (put at 60° C. in warm water bath for 1 hour before mixing). Mixing is achieved by mixing for five minutes using a Ultra-Turrax T25 Basic equipment (from IKA). After mixing, the mixture is put in a warm water bath at 60° C. for ±12 hours. A homogenous, viscous and sticky material is obtained.

In the same way as described above different ratios between the components can be used:

| | Weight % | | | | |
|---|---|---|---|---|---|
| Perfume composition | 40 | 50 | 60 | 70 | 80 |
| Lupasol ® WF | 12 | 10 | 8 | 6 | 4 |
| Hypro ™ RLP CTBN1300X18 | 48 | 40 | 32 | 24 | 16 |

| | Weight % | | | | | | | |
|---|---|---|---|---|---|---|---|---|
| Perfume composition | 50 | 50 | 50 | 50 | 50 | 50 | 50 | 50 |
| Lupasol ® WF | 2.5 | 5 | 7.5 | 10 | 12.5 | 15 | 17.5 | 20 |
| Hypro ™ RLP CTBN 1300X18 | 47.5 | 45 | 42.5 | 40 | 37.5 | 35 | 32.5 | 30 |

Examples 4-51

Product Formulation

Non-limiting examples of product formulations containing PRMs disclosed in the present specification perfume and amines summarized in the following table.

Examples 4-9

Granular Laundry Detergent Compositions for Hand Washing or Washing Machines, Typically Top-Loading Washing Machines

| | 4 (wt %) | 5 (wt %) | 6 (wt %) | 7 (wt %) | 8 (wt %) | 9 (wt %) |
|---|---|---|---|---|---|---|
| Linear alkylbenzenesulfonate | 20 | 22 | 20 | 15 | 19.5 | 20 |
| C$_{12-14}$ Dimethylhydroxyethyl ammonium chloride | 0.7 | 0.2 | 1 | 0.6 | 0.0 | 0 |
| AE3S | 0.9 | 1 | 0.9 | 0.0 | 0.4 | 0.9 |
| AE7 | 0.0 | 0.0 | 0.0 | 1 | 0.1 | 3 |
| Sodium tripolyphosphate | 5 | 0.0 | 4 | 9 | 2 | 0.0 |
| Zeolite A | 0.0 | 1 | 0.0 | 1 | 4 | 1 |
| 1.6R Silicate (SiO$_2$:Na$_2$O at ratio 1.6:1) | 7 | 5 | 2 | 3 | 3 | 5 |
| Sodium carbonate | 25 | 20 | 25 | 17 | 18 | 19 |
| Polyacrylate MW 4500 | 1 | 0.6 | 1 | 1 | 1.5 | 1 |
| Random graft copolymer[1] | 0.1 | 0.2 | 0.0 | 0.0 | 0.05 | 0.0 |
| Carboxymethyl cellulose | 1 | 0.3 | 1 | 1 | 1 | 1 |
| Stainzyme ® (20 mg active/g) | 0.1 | 0.2 | 0.1 | 0.2 | 0.1 | 0.1 |
| Protease (Savinase ®, 32.89 mg active/g) | 0.1 | 0.1 | 0.1 | 0.1 | | 0.1 |
| Amylase - Natalase ® (8.65 mg active/g) | 0.1 | 0.0 | 0.1 | 0.0 | 0.1 | 0.1 |
| Lipase - Lipex ® (18 mg active/g) | 0.03 | 0.07 | 0.3 | 0.1 | 0.07 | 0.4 |

-continued

|  | 4 (wt %) | 5 (wt %) | 6 (wt %) | 7 (wt %) | 8 (wt %) | 9 (wt %) |
|---|---|---|---|---|---|---|
| Fluorescent Brightener 1 | 0.06 | 0.0 | 0.06 | 0.18 | 0.06 | 0.06 |
| Fluorescent Brightener 2 | 0.1 | 0.06 | 0.1 | 0.0 | 0.1 | 0.1 |
| DTPA | 0.6 | 0.8 | 0.6 | 0.25 | 0.6 | 0.6 |
| $MgSO_4$ | 1 | 1 | 1 | 0.5 | 1 | 1 |
| Sodium Percarbonate | 0.0 | 5.2 | 0.1 | 0.0 | 0.0 | 0.0 |
| Sodium Perborate Monohydrate | 4.4 | 0.0 | 3.85 | 2.09 | 0.78 | 3.63 |
| NOBS | 1.9 | 0.0 | 1.66 | 0.0 | 0.33 | 0.75 |
| TAED | 0.58 | 1.2 | 0.51 | 0.0 | 0.015 | 0.28 |
| Sulphonated zinc phthalocyanine | 0.0030 | 0.0 | 0.0012 | 0.0030 | 0.0021 | 0.0 |
| S-ACMC | 0.1 | 0.0 | 0.0 | 0.0 | 0.06 | 0.0 |
| Direct Violet Dye (DV9 or DV99 or DV66) | 0.0 | 0.0 | 0.0003 | 0.0001 | 0.0001 | 0.0 |
| Additional Neat Perfume [2] | 0.5 | 0.5 | 0.5 | 0.5 | 0.5 | 0.5 |
| Amine [1] | 0.1 | 0.5 | 0.0 | 0.01 | 0.02 | 0.00 |
| Perfume Delivery System As Disclosed In The Present Specification Including Examples 2-3 | 0.05 | 0.0 | 0.1 | 0.0 | 0.2 | 0.4 |
| Perfume comprising one or more PRMs from Table 1 | 0.3 | 0.4 | 0.01 | 0.02 | 0.04 | 0.1 |
| Sulfate/Moisture | Balance | | | | | |

[1] One or more materials comprising an amine moiety as disclosed in the present specification.
[2] Optional.

Examples 10-15

Granular Laundry Detergent Compositions Typically for Front-Loading Automatic Washing Machines

|  | 10 (wt %) | 11 (wt %) | 12 (wt %) | 13 (wt %) | 14 (wt %) | 15 (wt %) |
|---|---|---|---|---|---|---|
| Linear alkylbenzenesulfonate | 8 | 7.1 | 7 | 6.5 | 7.5 | 7.5 |
| AE3S | 0 | 4.8 | 1.0 | 5.2 | 4 | 4 |
| C12-14 Alkylsulfate | 1 | 0 | 1 | 0 | 0 | 0 |
| AE7 | 2.2 | 0 | 2.2 | 0 | 0 | 0 |
| $C_{10-12}$ Dimethyl hydroxyethylammonium chloride | 0.75 | 0.94 | 0.98 | 0.98 | 0 | 0 |
| Crystalline layered silicate ($\delta$-$Na_2Si_2O_5$) | 4.1 | 0 | 4.8 | 0 | 0 | 0 |
| Zeolite A | 5 | 0 | 5 | 0 | 2 | 2 |
| Citric Acid | 3 | 5 | 3 | 4 | 2.5 | 3 |
| Sodium Carbonate | 15 | 20 | 14 | 20 | 23 | 23 |
| Silicate 2R ($SiO_2$:$Na_2O$ at ratio 2:1) | 0.08 | 0 | 0.11 | 0 | 0 | 0 |
| Soil release agent | 0.75 | 0.72 | 0.71 | 0.72 | 0 | 0 |
| Acrylic Acid/Maleic Acid Copolymer | 1.1 | 3.7 | 1.0 | 3.7 | 2.6 | 3.8 |
| Carboxymethylcellulose | 0.15 | 1.4 | 0.2 | 1.4 | 1 | 0.5 |
| Protease - Purafect ® (84 mg active/g) | 0.2 | 0.2 | 0.3 | 0.15 | 0.12 | 0.13 |
| Amylase - Stainzyme Plus ® (20 mg active/g) | 0.2 | 0.15 | 0.2 | 0.3 | 0.15 | 0.15 |
| Lipase - Lipex ® (18.00 mg active/g) | 0.05 | 0.15 | 0.1 | 0 | 0 | 0 |
| Amylase - Natalase ® (8.65 mg active/g) | 0.1 | 0.2 | 0 | 0 | 0.15 | 0.15 |
| Cellulase - Celluclean ™ (15.6 mg active/g) | 0 | 0 | 0 | 0 | 0.1 | 0.1 |
| TAED | 3.6 | 4.0 | 3.6 | 4.0 | 2.2 | 1.4 |
| Percarbonate | 13 | 13.2 | 13 | 13.2 | 16 | 14 |
| Na salt of Ethylenediamine-N,N'-disuccinic acid, (S,S) isomer (EDDS) | 0.2 | 0.2 | 0.2 | 0.2 | 0.2 | 0.2 |
| Hydroxyethane di phosphonate (HEDP) | 0.2 | 0.2 | 0.2 | 0.2 | 0.2 | 0.2 |
| $MgSO_4$ | 0.42 | 0.42 | 0.42 | 0.42 | 0.4 | 0.4 |
| Perfume | 0.5 | 0.6 | 0.5 | 0.6 | 0.6 | 0.6 |
| Suds suppressor agglomerate | 0.05 | 0.1 | 0.05 | 0.1 | 0.06 | 0.05 |
| Soap | 0.45 | 0.45 | 0.45 | 0.45 | 0 | 0 |
| Sulphonated zinc phthalocyanine (active) | 0.0007 | 0.0012 | 0.0007 | 0 | 0 | 0 |
| S-ACMC | 0.01 | 0.01 | 0 | 0.01 | 0 | 0 |
| Direct Violet 9 (active) | 0 | 0 | 0.0001 | 0.0001 | 0 | 0 |
| Additional Neat Perfume [2] | 0.5 | 0.5 | 0.5 | 0.5 | 0.5 | 0.5 |
| Amine [1] | 0.1 | 0.5 | 0.0 | 0.01 | 0.02 | 0.00 |
| Perfume Delivery System As Disclosed In The Present Specification Including Examples 2-3 | 0.05 | 0.0 | 0.1 | 0.0 | 0.2 | 0.4 |

-continued

|  | 10 (wt %) | 11 (wt %) | 12 (wt %) | 13 (wt %) | 14 (wt %) | 15 (wt %) |
|---|---|---|---|---|---|---|
| Perfume comprising one or more PRMs from Table 1 | 0.3 | 0.4 | 0.01 | 0.02 | 0.04 | 0.1 |
| Sulfate/Water & Miscellaneous | Balance | | | | | |

[1] One or more materials comprising an amine moiety as disclosed in the present specification.
[2] Optional.

The typical pH is about 10.

Examples 16-22

Heavy Duty Liquid Laundry Detergent Compositions

|  | 16 (wt %) | 17 (wt %) | 18 (wt %) | 19 (wt %) | 20 (wt %) | 21 (wt %) | 22 (wt %) |
|---|---|---|---|---|---|---|---|
| AES $C_{12-15}$ alkyl ethoxy (1.8) sulfate | 11 | 10 | 4 | 6.32 | 0 | 0 | 0 |
| AE3S | 0 | 0 | 0 | 0 | 2.4 | 0 | 0 |
| Linear alkyl benzene sulfonate/sulfonic acid | 1.4 | 4 | 8 | 3.3 | 5 | 8 | 19 |
| HSAS | 3 | 5.1 | 3 | 0 | 0 | 0 | 0 |
| Sodium formate | 1.6 | 0.09 | 1.2 | 0.04 | 1.6 | 1.2 | 0.2 |
| Sodium hydroxide | 2.3 | 3.8 | 1.7 | 1.9 | 1.7 | 2.5 | 2.3 |
| Monoethanolamine | 1.4 | 1.49 | 1.0 | 0.7 | 0 | 0 | To pH 8.2 |
| Diethylene glycol | 5.5 | 0.0 | 4.1 | 0.0 | 0 | 0 | 0 |
| AE9 | 0.4 | 0.6 | 0.3 | 0.3 | 0 | 0 | 0 |
| AE8 | 0 | 0 | 0 | 0 | 0 | 0 | 20.0 |
| AE7 | 0 | 0 | 0 | 0 | 2.4 | 6 | 0 |
| Chelant (HEDP) | 0.15 | 0.15 | 0.11 | 0.07 | 0.5 | 0.11 | 0.8 |
| Citric Acid | 2.5 | 3.96 | 1.88 | 1.98 | 0.9 | 2.5 | 0.6 |
| $C_{12-14}$ dimethyl Amine Oxide | 0.3 | 0.73 | 0.23 | 0.37 | 0 | 0 | 0 |
| $C_{12-18}$ Fatty Acid | 0.8 | 1.9 | 0.6 | 0.99 | 1.2 | 0 | 15.0 |
| 4-formyl-phenylboronic acid | 0 | 0 | 0 | 0 | 0.05 | 0.02 | 0.01 |
| Borax | 1.43 | 1.5 | 1.1 | 0.75 | 0 | 1.07 | 0 |
| Ethanol | 1.54 | 1.77 | 1.15 | 0.89 | 0 | 3 | 7 |
| A compound having the following general structure: bis(($C_2H_5O$)($C_2H_4O$)n)($CH_3$)—$N^+$—$C_xH_{2x}$—$N^+$—($CH_3$)-bis(($C_2H_5O$)($C_2H_4O$)n), wherein n = from 20 to 30, and x = from 3 to 8, or sulphated or sulphonated variants thereof | 0.1 | 0 | 0 | 0 | 0 | 0 | 2.0 |
| Ethoxylated ($EO_{15}$) tetraethylene pentamine | 0.3 | 0.33 | 0.23 | 0.17 | 0.0 | 0.0 | 0 |
| Ethoxylated Polyethylenimine | 0 | 0 | 0 | 0 | 0 | 0 | 0.8 |
| Ethoxylated hexamethylene diamine | 0.8 | 0.81 | 0.6 | 0.4 | 1 | 1 | 0 |
| 1,2-Propanediol | 0.0 | 6.6 | 0.0 | 3.3 | 0.5 | 2 | 8.0 |
| Fluorescent Brightener | 0.2 | 0.1 | 0.05 | 0.3 | 0.15 | 0.3 | 0.2 |
| Hydrogenated castor oil derivative structurant | 0.1 | 0 | 0 | 0 | 0 | 0 | 0.1 |
| Perfume | 1.6 | 1.1 | 1.0 | 0.8 | 0.9 | 1.5 | 1.6 |
| Protease (40.6 mg active/g) | 0.8 | 0.6 | 0.7 | 0.9 | 0.7 | 0.6 | 1.5 |
| Mannanase: Mannaway ® (25 mg active/g) | 0.07 | 0.05 | 0.045 | 0.06 | 0.04 | 0.045 | 0.1 |
| Amylase: Stainzyme ® (15 mg active/g) | 0.3 | 0 | 0.3 | 0.1 | 0 | 0.4 | 0.1 |
| Amylase: Natalase ® (29 mg active/g) | 0 | 0.2 | 0.1 | 0.15 | 0.07 | 0 | 0.1 |
| Xyloglucanase (Whitezyme ®, 20 mg active/g) | 0.2 | 0.1 | 0 | 0 | 0.05 | 0.05 | 0.2 |
| Lipex ® (18 mg active/g) | 0.4 | 0.2 | 0.3 | 0.1 | 0.2 | 0 | 0 |
| Additional Neat Perfume [2] | 0.5 | 0.5 | 0.5 | 0.5 | 0.5 | 0.5 | 0.5 |
| Amine [1] | 0.1 | 0.5 | 0.0 | 0.01 | 0.02 | 0.00 | 0.07 |
| Perfume Delivery System As Disclosed In The Present Specification Including Examples 2-3 | 0.05 | 0.0 | 0.1 | 0.0 | 0.2 | 0.4 | 0.0 |

-continued

|  | 16 (wt %) | 17 (wt %) | 18 (wt %) | 19 (wt %) | 20 (wt %) | 21 (wt %) | 22 (wt %) |
|---|---|---|---|---|---|---|---|
| Perfume comprising one or more PRMs from Table 1 | 0.7 | 0.5 | 0.8 | 0.05 | 0.6 | 0.1 | 0.6 |
| *Water, dyes & minors | | | | Balance | | | |

*Based on total cleaning and/or treatment composition weight, a total of no more than 12% water
(1) One or more materials comprising an amine moiety as disclosed in the present specification.
(2) Optional.

Examples 23-24

Unit Dose Compositions

| | Example of Unit Dose detergents | |
|---|---|---|
| | 23 | 24 |
| C14-C15 alkyl poly ethoxylate (8) | 12 | — |
| C12-C14 alkyl poly ethoxylate (7) | 1 | 14 |
| C12-C14 alkyl poly ethoxylate (3) sulfate Mono EthanolAmine salt | 8.4 | 9 |
| Linear Alkylbenzene sulfonic acid | 15 | 16 |
| Citric Acid | 0.6 | 0.5 |
| C12-C18 Fatty Acid | 15 | 17 |
| Enzymes | 1.5 | 1.2 |
| PEI 600 EO20 | 4 | — |
| Diethylene triamine penta methylene phosphonic acid or HEDP | 1.3 | — |
| Fluorescent brightener | 0.2 | 0.3 |
| Hydrogenated Castor Oil | 0.2 | 0.2 |
| 1,2 propanediol | 16 | 12 |
| Glycerol | 6.2 | 8.5 |
| Sodium hydroxide | — | 1 |
| Mono Ethanol Amine | 7.9 | 6.1 |
| Dye | Present | Present |
| PDMS | — | 2.7 |
| Potassium sulphite | 0.2 | 0.2 |
| Additional Neat Perfume(2) | 0.5 | 0.5 |
| Amine(1) | 0.1 | 0.5 |
| Perfume Delivery System As Disclosed In The Present Specification Including Examples 2-3 | 0.05 | 0.0 |
| Perfume comprising one or more PRMs from Table 1 | 0.3 | 0.4 |
| Water | Up to 100p | Up to 100 |

(1)One or more materials comprising an amine moiety as disclosed in the present specification.
(2)Optional.

Example 25-30

Bleach & Laundry Additive Detergent Formulations

| Ingredients | 25 | 26 | 27 | 28 | 29 | 30 |
|---|---|---|---|---|---|---|
| AES | 11.3 | 6.0 | 15.4 | 16.0 | 12.0 | 10.0 |
| LAS | 25.6 | 12.0 | 4.6 | — | — | 26.1 |
| MEA-HSAS | — | — | — | 3.5 | — | — |
| DTPA: Diethylene triamine pentaacetic acid | 0.51 | — | 1.5 | — | — | 2.6 |
| 4,5-Dihydroxy-1,3-benzenedisulfonic acid disodium salt | 1.82 | — | — | — | — | 1.4 |
| 1,2-propandiol | — | 10 | — | — | — | 15 |
| Copolymer of dimethylterephthalate, 1,2-propylene glycol, methyl capped PEG | 2.0 | | | | | |
| Poly(ethyleneimine) ethoxylated, PEI600 E20 | | 1.8 | | | | |
| Acrylic acid/maleic acid copolymer | | | | 2.9 | | |
| Acusol 880 (Hydrophobically Modified Non-Ionic Polyol) | | | | 2.0 | 1.8 | 2.9 |
| Protease (55 mg/g active) | — | — | — | — | 0.1 | 0.1 |
| Amylase (30 mg/g active) | — | — | — | — | — | 0.02 |
| Brightener | 0.21 | — | — | 0.15 | — | 0.18 |
| Dye or mixture or dyes selected from Examples 1-28 in Table 1. | 0.01 | 0.005 | 0.006 | 0.002 | 0.007 | 0.008 |
| Additional Neat Perfume (2) | 0.5 | 0.5 | 0.5 | 0.5 | 0.5 | 0.5 |
| Amine (1) | 0.1 | 0.5 | 0.0 | 0.01 | 0.02 | 0.00 |
| Perfume Delivery System As Disclosed In The Present Specification Including Examples 2-3 | 0.05 | 0.0 | 0.1 | 0.0 | 0.2 | 0.4 |
| Perfume comprising one or more PRMs from Table 1 | 0.3 | 0.4 | 0.01 | 0.02 | 0.04 | 0.1 |
| water, other optional agents/components* | to 100% balance | to 100% balance | to 100% balance | to 100% balance | to 100% balance | to 100% balance |

(3) One or more materials comprising an amine moiety as disclosed in the present specification.
(4) Optional.
*Other optional agents/components include suds suppressors, structuring agents such as those based on Hydrogenated Castor Oil (preferably Hydrogenated Castor Oil, Anionic Premix), solvents and/or Mica pearlescent aesthetic enhancer.

Raw Materials and Notes for Composition Examples
  LAS is linear alkylbenzenesulfonate having an average aliphatic carbon chain length $C_9$-$C_{15}$ supplied by Stepan, Northfield, Ill., USA or Huntsman Corp. (HLAS is acid form). $C_{12-14}$ Dimethylhydroxyethyl ammonium chloride, supplied by Clariant GmbH, Germany
  AE3S is $C_{12-15}$ alkyl ethoxy (3) sulfate supplied by Stepan, Northfield, Ill., USA
  AE7 is $C_{12-15}$ alcohol ethoxylate, with an average degree of ethoxylation of 7, supplied by Huntsman, Salt Lake City, Utah, USA
  AES is $C_{10-18}$ alkyl ethoxy sulfate supplied by Shell Chemicals.
  AE9 is $C_{12-13}$ alcohol ethoxylate, with an average degree of ethoxylation of 9, supplied by Huntsman, Salt Lake City, Utah, USA
  HSAS or HC1617HSAS is a mid-branched primary alkyl sulfate with average carbon chain length of about 16-17
  Sodium tripolyphosphate is supplied by Rhodia, Paris, France
  Zeolite A is supplied by Industrial Zeolite (UK) Ltd, Grays, Essex, UK
  1.6R Silicate is supplied by Koma, Nestemica, Czech Republic
  Sodium Carbonate is supplied by Solvay, Houston, Tex., USA
  Polyacrylate MW 4500 is supplied by BASF, Ludwigshafen, Germany
  Carboxymethyl cellulose is Finnfix® V supplied by CP Kelco, Arnhem, Netherlands
  Suitable chelants are, for example, diethylenetetraamine pentaacetic acid (DTPA) supplied by Dow Chemical, Midland, Mich., USA or Hydroxyethane di phosphonate (HEDP) supplied by Solutia, St Louis, Mo., USA Bagsvaerd, Denmark
  Savinase®, Natalase®, Stainzyme®, Lipex®, Celluclean™, Mannaway® and Whitezyme® are all products of Novozymes, Bagsvaerd, Denmark.
  Proteases may be supplied by Genencor International, Palo Alto, Calif., USA (e.g. Purafect Prime®) or by Novozymes, Bagsvaerd, Denmark (e.g. Liquanase®, Coronase®).
  Fluorescent Brightener 1 is Tinopal® AMS, Fluorescent Brightener 2 is Tinopal® CBS-X, Sulphonated zinc phthalocyanine and Direct Violet 9 is Pergasol® Violet BN-Z all supplied by Ciba Specialty Chemicals, Basel, Switzerland
  Sodium percarbonate supplied by Solvay, Houston, Tex., USA
  Sodium perborate is supplied by Degussa, Hanau, Germany
  NOBS is sodium nonanoyloxybenzenesulfonate, supplied by Future Fuels, Batesville, USA
  TAED is tetraacetylethylenediamine, supplied under the Peractive® brand name by Clariant GmbH, Sulzbach, Germany
  S-ACMC is carboxymethylcellulose conjugated with C.I. Reactive Blue 19, sold by Megazyme, Wicklow, Ireland under the product name AZO-CM-CELLULOSE, product code S-ACMC.
  Soil release agent is Repel-o-tex® PF, supplied by Rhodia, Paris, France
  Acrylic Acid/Maleic Acid Copolymer is molecular weight 70,000 and acrylate:maleate ratio 70:30, supplied by BASF, Ludwigshafen, Germany
  Na salt of Ethylenediamine-N,N'-disuccinic acid, (S,S) isomer (EDDS) is supplied by Octel, Ellesmere Port, UK
  Hydroxyethane di phosphonate (HEDP) is supplied by Dow Chemical, Midland, Mich., USA
  Suds suppressor agglomerate is supplied by Dow Corning, Midland, Mich., USA
  HSAS is mid-branched alkyl sulfate as disclosed in U.S. Pat. No. 6,020,303 and U.S. Pat. No. 6,060,443
  $C_{12-14}$ dimethyl Amine Oxide is supplied by Procter & Gamble Chemicals, Cincinnati, USA
  Random graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40:60 and no more than 1 grafting point per 50 ethylene oxide units.
  Ethoxylated polyethyleneimine is polyethyleneimine (MW=600) with 20 ethoxylate groups per —NH.
  Cationic cellulose polymer is LK400, LR400 and/or JR30M from Amerchol Corporation, Edgewater N.J.
  Note: all enzyme levels are expressed as % enzyme raw material
  The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Example 31

Shampoo Formulations

| Ingredient | |
|---|---|
| Ammonium Laureth Sulfate (AE$_3$S) | 6.00 |
| Ammonium Lauryl Sulfate (ALS) | 10.00 |
| Laureth-4 Alcohol | 0.90 |
| Trihydroxystearin[7] | 0.10 |
| Perfume comprising one or more PRMs from Table 1 | 0.60 |
| Sodium Chloride | 0.40 |
| Citric Acid | 0.04 |
| Sodium Citrate | 0.40 |
| Sodium Benzoate | 0.25 |
| Ethylene Diamine Tetra Acetic Acid | 0.10 |
| Dimethicone[9,10,11] | 1.00[9] |
| Water and Minors (QS to 100%) | Balance |

Example 32-34

Fine Fragrance Formulations

| Ingredient | 32 | 33 | 34 |
|---|---|---|---|
| Cyclic oligosaccharide | 0 | 5 | 10 |
| Ethanol | 90 | 75 | 80 |
| Perfume comprising one or more PRMs from Table 1 | 10 | 20 | 10 |

Example 35-48

Dentifrice Containing Sensate

| Ingredient | 35 | 36 | 37 | 38 | 39 | 40 | 41 | 42 | 43 |
|---|---|---|---|---|---|---|---|---|---|
| Calcium Peroxide | | | 0.1 | | | | | | |
| Carbomer 956 | 0.2 | | | 0.3 | 0.2 | 0.2 | 0.2 | 0.2 | 0.2 |
| CMC | | 0.75 | 0.2 | | | 1.0 | 1.0 | 1.0 | 1.0 |
| Color Solution (1%) | 0.05 | 0.05 | 0.5 | 0.75 | 0.18 | 0.02 | 0.25 | 0.05 | 0.05 |
| Wintergreen Spice Flavor | | | | | 0.15 | | | | |
| Fruit Mint Flavor | | 0.55 | | | | | | | |
| Mint Flavor | 0.59 | | 0.45 | | 0.42 | 1.0 | 1.2 | 1.0 | 1.0 |
| Cinnamon Flavor | | | | 0.5 | | | | | |
| Vanillyl Butyl Ether | | | | | 0.02 | | | | |
| WS-23 | | | 0.1 | 0.05 | 0.1 | | | | |
| WS-3 | | | 0.2 | 0.05 | 0.2 | | | | |
| MGA | | | | 0.2 | | | | | |
| Menthol | 0.52 | 0.55 | 0.56 | 0.15 | 0.58 | | | | |
| Sensate comprising one or more PRMs from Table 1 | 0.01 | 0.03 | 0.015 | 0.004 | 0.01 | 0.01 | 0.03 | 0.008 | 0.02 |
| Potassium Sorbate | | | | | | 0.004 | 0.008 | 0.004 | 0.004 |
| Poloxamer 407 | | | 1.0 | | 0.2 | 0.2 | 0.2 | 0.2 | 0.2 |
| Polyethylene Glycol 300 | 3.0 | 3.0 | | 3.0 | | | | | |
| Polyethylene Glycol 600 | | | 2.3 | | | | | | |
| Propylene Glycol | | | 10.0 | | | | | | |
| Saccharin Sodium | 0.46 | 0.5 | 0.45 | 0.4 | 0.58 | 0.4 | 0.4 | 0.4 | 0.4 |
| Sucralose | | | | | | | 0.02 | 0.02 | 0.02 |
| Silica Abrasive | 22.0 | 31.0 | 20.0 | 21.0 | 17.0 | 15.0 | 15.0 | 15.0 | 15.0 |
| Sodium Benzoate | | | | | | 0.004 | 0.004 | 0.004 | 0.004 |
| Silica Thickening | | | 2.0 | | | 7.0 | 7.0 | 7.0 | 7.0 |
| Sodium Bicarbonate | | 1.5 | 9.0 | | | | | | |
| Sodium Carbonate | | 0.5 | | | | | | | |
| NaOH 50% soln | | | 1.74 | 2.2 | | 2.0 | 2.0 | 2.0 | 2.0 |
| Na Lauryl Sulfate (27.9% soln) | 4.0 | 5.0 | 3.0 | 4.0 | 4.0 | | | 3.0 | 2.0 |
| Stannous Fluoride | 0.454 | 0.454 | | | | | | | |
| Sodium Fluoride | | | | | | 0.243 | 0.243 | 0.243 | |
| Sodium MFP | | | 0.76 | 0.76 | 0.76 | 0.76 | | | |
| Glycerin USP 99.7% | 9.0 | 11.9 | 33.0 | 9.0 | | | | | |
| Sorbitol Soln USP | 24.3 | 24.5 | 4.0 | 44.7 | 56.9 | 43.0 | 43.0 | 40.0 | 38.0 |
| Tetra Na Pyrophosphate Anhydrous | 2.05 | 5.045 | 3.85 | | 3.85 | | | | |
| Tetra Potassium Pyrophosphate (60% Soln) | 6.38 | | | | | | | | |
| Na Acid Pyrophosphate | 2.1 | | | 4.0 | 1.0 | 4.3 | 4.5 | 4.5 | 2.0 |
| Alkyl Phosphate | | | | | | 3.5 | 6.7 | 3.5 | 3.5 |
| Cocamidopropyl Betaine (30% Soln) | | | | | | 3.5 | | | |
| TitaniumDioxide | 0.5 | | 1.0 | | 0.25 | 0.3 | 0.3 | 0.2 | 0.2 |
| TiO2/Carnauba Wax Prills | | 0.6 | | 0.3 | | | | | |
| Xanthan Gum | 0.6 | | 0.4 | 0.45 | 0.7 | 0.3 | 0.3 | 0.3 | 0.3 |
| Water Purified USP | QS | QS | QS | QS | QS | QS | QS | QS | QS |

| Ingredient | 44 | 45 | 46 | 47 | 48 |
|---|---|---|---|---|---|
| Calcium Carbonate | | | | 40.0 | |
| Dibasic Calcium Phosphate Dihydrate | | | 35.0 | | |
| Silica Abrasive | 24.0 | 12.5 | | | 17.0 |
| Phytic Acid | | 0.8 | | | 2.0 |
| Gantrez S-97 | | | 2.0 | | |
| Color Solution (1%) | 0.05 | 0.05 | | | 0.05 |
| Saccharin sodium | 0.47 | 0.25 | 0.3 | 0.3 | 0.58 |
| Spice Mint Flavor | | | | 1.0 | |
| Wintergreen Spice Flavor | | 1.2 | | | 0.15 |
| Mint Flavor | | 0.3 | 0.6 | 0.5 | 0.42 |
| Cinnamon Flavor | 0.18 | | | | |
| WS-23 Coolant | 0.03 | | | | 0.02 |
| WS-3 Coolant | 0.03 | | | | 0.02 |
| MGA | 0.08 | 0.08 | | | |
| Menthol | 0.38 | 0.24 | 0.2 | 0.5 | 0.58 |
| Sensate comprising one or more PRMs from Table 1 | 0.08 | 0.005 | 0.004 | 0.008 | 0.01 |
| Glycerin | 16.5 | | 15.0 | | |
| Sorbitol solution | 10.5 | 33.0 | 11.5 | 14.0 | 57.0 |
| Poloxamer 407 | | | | | 0.2 |
| Polyethylene Glycol 300 | | | | 2.5 | |
| Polyethylene Glycol 600 | | | 3.0 | | |
| Carbomer | | 0.3 | | | 0.2 |

-continued

| | | | | | |
|---|---|---|---|---|---|
| CMC 7M8SF | 1.0 | | 1.0 | 1.0 | |
| HEC 250MX | | 0.5 | | | |
| Sodium Lauryl Sulfate (27.9% soln) | 7.5 | 7.0 | 5.5 | 7.0 | 4.0 |
| NaOH 50% soln | | 1.0 | | | |
| Sodium Monofluorophosphate | 0.76 | | 0.76 | 0.76 | 0.76 |
| Sodium Fluoride | | 0.32 | | | |
| Sodium Gluconate | | 1.0 | | | |
| Stannous Chloride Dihydrate | | 1.0 | | | |
| Zinc Citrate | | 0.5 | | | |
| Potassium Nitrate | 5.0 | | | | |
| Sodium Phosphate, Tribasic | 3.2 | | | | |
| Tetra Sodium Pyrophosphate, Anhydrous | | | 0.5 | 0.5 | 3.85 |
| Sodium Acid Pyrophosphate | | | | | 1.0 |
| TitaniumDioxide | 0.5 | 0.5 | | | 0.25 |
| Xanthan Gum (Keltro 1000 | | | | 0.5 | 0.7 |
| Carrageenan | | 0.5 | | | |
| Water, Purified, USP | QS | QS | QS | QS | QS |

Example 49-51

Mouthrinse Containing Sensate

| Ingredient | 49 | 50 | 51 |
|---|---|---|---|
| Ethanol USP 190 proof | 15 | 15 | 15 |
| Glycerin | 7.5 | 7.5 | 7.5 |
| Polysorbate 80 NF | 0.12 | 0.12 | 0.12 |
| Flavor' | 0.16 | 0.16 | 0.16 |
| Saccharin sodium | 0.067 | 0.067 | 0.06 |
| Color solution | 0.04 | 0.04 | 0.04 |
| Sensate comprising one or more PRMs from Table 1 | 0.03 | 0.017 | 1 |
| Calcium chloride | 0.025 | 0.025 | 0.025 |
| Cetylpyridinium chloride | 0.045 | 0.045 | 0.045 |
| Benzoic acid | 0.005 | 0.005 | 0.005 |
| Sodium benzoate | 0.054 | 0.054 | 0.054 |
| Water | QS | QS | QS |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A molecule selected from the group consisting of:
a) a molecule having the following structure

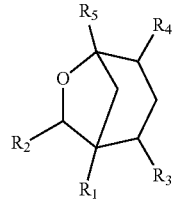

wherein $R_1$, $R_4$ and $R_5$ are each independently selected from the group consisting of: a straight or branched $C_1$-$C_6$ alkyl moiety; a straight or branched $C_2$-$C_6$ alkenyl moiety; and a straight or branched $C_2$-$C_6$ alkyne moiety; and wherein $R_2$ and $R_3$ are each independently selected from the group consisting of: hydrogen; a straight or branched $C_1$-$C_6$ alkyl moiety; a straight or branched $C_2$-$C_6$ alkenyl moiety; and a straight or branched $C_2$-$C_6$ alkyne moiety;
b) stereomers of said molecule; and
c) mixtures thereof.

2. A composition comprising, based on total composition weight, at least 0.00001% of one or more molecules according to claim 1 and an optional adjunct material.

3. A composition according to claim 2, said composition comprising based on total composition weight, from about 0.0001% to about 25% of one or more molecules according to claim 1; and an adjunct ingredient said composition being a consumer product.

4. A composition according to claim 2, said composition, being a cleaning and treatment composition.

5. A composition according to claim 2, said composition being a fabric and/or hard surface cleaning and/or treatment composition.

6. A composition according to claim 2, said composition being a detergent, said detergent comprising, based on total detergent weight, from about 0.00001% to about 25% of one or more molecules according to claim 1; and an adjunct ingredient.

7. A composition according to claim 2, said composition being a highly compacted consumer product, said highly compacted consumer product comprising, based on total highly compacted consumer product weight, from about 0.00001% to about 25% of one or more molecules according to claim 1; and an adjunct ingredient.

8. A highly compacted consumer product according to claim 7, said highly compacted consumer product being a highly compacted detergent.

9. The composition of claim 2, said composition being a perfume delivery system selected from a polymer assisted delivery system; a molecule-assisted delivery system; a fiber-assisted delivery system; a cyclodextrin delivery system; a starch encapsulated accord; and/or an inorganic carrier delivery system.

10. A perfume delivery system according to claim 9, said perfume delivery system being a nanocapsule or a microcapsule comprising, based on total nanocapsule or microcapsule weight, at least 0.001% of one or more molecules according to claim 1.

11. A perfume delivery system according to claim 9, said perfume delivery system being a starch encapsulated accord comprising, based on total starch encapsulate or starch agglomerate weight, at least 0.001% of one or more molecules according to claim 1.

12. A perfume delivery system according to claim 9, said perfume delivery system being a cyclodextrin delivery system comprising based on total cyclodextrin delivery system weight, at least 0.001% of one or more molecules according to claim 1.

13. A perfume delivery system according to claim 9, said perfume delivery system being a polymer assisted delivery matrix system comprising, based on total polymer assisted delivery matrix system weight, at least 0.001% of one or more molecules according to claim 1.

14. A consumer product comprising, based on total consumer product weight, at least 0.001% of a perfume delivery system selected from the perfume delivery systems of any one of claims 9-13 and mixtures thereof.

15. An oral care composition comprising, based on total composition weight, at least 0.001% of one or more molecules according to claim 1 and an adjunct ingredient selected from the group consisting of stannous, zinc, potassium, calcium, or copper salts, antibacterial agents, anti-tartar agents, breath reduction agents, chelants, structuring agents, TRPV1 or TRPA1 agonists, TRPV1 or TRPA1 antagonists, TRPM8 enhancers, flavor, tooth sensitivity actives, caries actives, abrasives, sorbitol, menthol, bitter blockers, anionic surfactant, cationic surfactant, nonionic surfactant, or combinations thereof.

* * * * *